(12) United States Patent
Uno (10) Patent No.: US 10,526,324 B2
(45) Date of Patent: Jan. 7, 2020

(54) CRYSTALS OF AZABICYCLIC COMPOUND

(71) Applicant: TAIHO PHARMACEUTICAL CO., LTD., Chiyoda-ku (JP)

(72) Inventor: Takao Uno, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/572,398

(22) PCT Filed: May 11, 2016

(86) PCT No.: PCT/JP2016/063989
§ 371 (c)(1),
(2) Date: Nov. 7, 2017

(87) PCT Pub. No.: WO2016/181990
PCT Pub. Date: Nov. 17, 2016

(65) Prior Publication Data
US 2018/0148443 A1    May 31, 2018

(30) Foreign Application Priority Data
May 12, 2015 (JP) ................................ 2015-097521

(51) Int. Cl.
| C07D 471/04 | (2006.01) |
| A61K 31/4439 | (2006.01) |
| A61P 35/00 | (2006.01) |

(52) U.S. Cl.
CPC ........ *C07D 471/04* (2013.01); *A61K 31/4439* (2013.01); *A61P 35/00* (2018.01); *C07B 2200/13* (2013.01)

(58) Field of Classification Search
CPC .................................................. C07D 471/04
See application file for complete search history.

(56) References Cited

U.S. PATENT DOCUMENTS

| 8,779,142 | B2 * | 7/2014 | Kitade ................. C07D 209/08 546/118 |
| 2012/0108589 | A1 | 5/2012 | Kitade et al. |
| 2013/0296320 | A1 | 11/2013 | Kitade et al. |
| 2014/0303162 | A1 | 10/2014 | Kitade et al. |

FOREIGN PATENT DOCUMENTS

| CN | 103313970 A | 9/2013 |
| RU | 2 357 967 C2 | 6/2009 |
| WO | WO 2004/024728 A2 | 3/2004 |
| WO | 2011/004610 A1 | 1/2011 |
| WO | 2012/093708 A1 | 7/2012 |

OTHER PUBLICATIONS

Peterson et. al. "Expanding the Scope of Crystal Form Evaluation in Pharmaceutical Science" Journal of Pharmacy & Pharmaceutical Science 2006 (9(3):317-326.*
Miller et. al. "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.*
Simone, Oncology: Introduction, Cecil Textbook of Medicine, 20th Edition, 1996 vol. 1, pp. 1004-1010.*
Dymock et al. "Inhibitors of HSP90 and Other Chaperones for the Treatment of Cancer", Expert Opinion on Therapeutic Patents 2004, 14(6), 837-847.*
Bagatell et al. "Altered HSP90 Function in Cancer: A Unique Therapeutic Opportunity", Molecular Cancer Therapy, 2004 1021-1030.*
Whitesell et al. "Targeting HSP90 Function to Treat Cancer: Much More to Be Learned", Heat Shock Proteins in Cancer, 2007, 253-274.*
Trepel et al. "Targeting the Dynamic HSP90 Complex in Cancer", Nat. Rev. Cancer, 10(8); 2010:537-549.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Johnson, et. al. "Relationships between drug activity in NCI preclinical in vitro and in vivo models and early clinical trials." British Journal of Cancer 2001, 84, 1424-1431.*
Ledford "US cancer institute overhauls cell lines" Nature Feb. 25, 2016 vol. 530 p. 391.*
International Search Report dated Jul. 12, 2016, in PCT/JP2016/063989, filed May 11, 2016.
Hirayama, "Yuki Kagobutsu Kessho Sakusei Handbook", Kodansha Ltd., 2008, 67 pages, with partial English translation.
Byrn et al., "Pharmaceutical Solids: A Strategic Approach to Regulatory Considerations", Pharmaceutical Research, vol. 12, No. 7, 1995, pp. 945-954.
Savjani et al., "Drug Solubility: Importance and Enhancement Techniques", International Scholarly Research Network ISRN Pharmaceutics, vol. 2012, 2012, pp. 1-10.
First Office Action dated Jun. 20, 2019 in Chinese Patent Application No. 201680027213.0 (with English translation).
Ohkubo et al., "TAS-116, a Highly Selective Inhibitor of Heat Shock Protein 90α and β, Demonstrates Potent Antitumor Activity and Minimal Ocular Toxicity in Preclinical Models", Mol. Cancer Ther. 14(1):14-22 (2015).

(Continued)

*Primary Examiner* — David K O'Dell
(74) *Attorney, Agent, or Firm* — Oblon, McClelland, Maier & Neustadt, L.L.P.

(57) ABSTRACT

Provided are crystals of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide which are stable and show excellent oral absorbability.
The crystals are Form II crystals of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide showing an X-ray powder diffraction spectrum having at least three characteristic diffraction peaks at angles (2θ±0.2°) selected from the group consisting of 7.7°, 8.0°, 11.1°, 12.5°, 12.9°, 15.2°, 15.8°, 17.2°, 19.0°, 22.5°, 26.1°, and 27.4°.

6 Claims, 4 Drawing Sheets

(56) References Cited

OTHER PUBLICATIONS

Office Action dated Oct. 30, 2018 in Russian Patent Application No. 2017142958, with English translation, 10 pages.
Office Action dated Oct. 24, 2018; in U.S. Reissue U.S. Appl. No. 96/000,268.
Request for Supplemental Examination U.S. Appl. No. 96/000,268, filed Aug. 2, 2018, 34 pages.
Exhibit 1 filed in the Supplemental U.S. Appl. No. 96/000,268, filed Aug. 2, 2018 "Clinical Study Report", Taiho Pharmaceutical Co., Ltd., 2007, 219 pages.
Exhibit 2 filed in the Supplemental U.S. Appl. No. 96/000,268, filed Aug. 2, 2018 U.S. Pat. No. 7,799,783, issued Sep. 21, 2010, 9 pages.
Exhibit 3 filed in the Supplemental U.S. Appl. No. 96/000,268, filed Aug. 2, 2018 Japanese Priority Document Application No. 2013-126567, filed Jun. 17, 2017, 41 pages (with certified English translation).
Exhibit 4 filed in the Supplemental U.S. Appl. No. 96/000,268, filed Aug. 2, 2018 M.D. Anderson Cente Spronsord Clinical Study, 16 pages.
Exhibit 5 filed in the Supplemental U.S. Appl. No. 96/000,268, filed Aug. 2, 2018 Confidentiality Agreement between Covance Inc. and Taiho Pharmaceutical Co., Ltd., 1998, 4 pages.
Exhibit 6 filed in the Supplemental U.S. Appl. No. 96/000,268, filed Aug. 2, 2018 Tae Won Kim, "465PD—TERRA: a randomized, double-blind, placebo controlled phase 3 study of TAS-102 in Asian patients with metastatic colorectal cancer", 2016, 2 pages.
Exhibit 7 filed in the Supplemental U.S. Appl. No. 96/000,268, filed Aug. 2, 2018 Taiho Feb. 27, 2013 Press Release Regarding Clinical Trials, 4 pages (with English translation).
Exhibit 8 filed in the Supplemental U.S. Appl. No. 96/000,268, filed Aug. 2, 2018 "Safety and Pharmacokinetics (pk) of an Antitumor/antiangiogenic Agent, TAS-102: A (pts) With Solid Tumors", Abstract presented May 12, 2001, 2 pages.
Exhibit 9 filed in the Supplemental U.S. Appl. No. 96/000,268, filed Aug. 2, 2018 "Global Investigator's Brochure for TAS-102", Version G 9.0, Release date May 21, 2018, 166 pages.

\* cited by examiner

[Figure 1]
FORM I CRYSTAL

[Figure 2]
FORM II CRYSTAL

CRYSTALS OF AZABICYCLIC COMPOUND

FIELD OF THE INVENTION

The present invention relates to a novel crystal of an azabicyclic compound which is stable and has excellent oral absorbability, and is useful as an antitumor agent.

BACKGROUND OF THE INVENTION

In general, when a compound is used as an effective active ingredient of a pharmaceutical, the chemical and physical stability of the compound is required in order to keep the quality stable and/or facilitate the storage management. Therefore, the obtained compound is preferably in a stable crystal form and in general the most stable crystal form is often selected as a drug substance for a pharmaceutical.

So far, a plurality of HSP90 inhibitors have been reported as an antitumor agent, for example, Patent Document 1 and 2 describe 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide (hereinafter also referred to as "Compound 1") as a compound which has excellent HSP90 inhibitory action and shows antitumor activity.

Meanwhile, although a pharmaceutical composition for oral administration requires in general not only the stability of an effective ingredient, but also excellent absorbability on oral administration, Patent Document 1 and 2 do not describe any crystals of Compound 1, nor the stability and oral absorbability of the crystals.

CITATION LIST

Patent Document

[Patent Document 1]
International Publication No. WO2012/093708
[Patent Document 2]
International Publication No. WO2011/004610

SUMMARY OF THE INVENTION

Problem to be Solved by the Invention

An object of the present invention is to provide a crystal of Compound 1 useful as an antitumor agent which is stable and has excellent oral absorbability.

Means for Solving the Problem

To achieve the object, the present inventor synthesized Compound 1 according to the method of manufacturing described in Patent Document 1 to obtain a Form I crystal of Compound 1. However, as described in Examples below, the Form I crystal had problems in oral absorbability, and thus they further investigated the crystallization conditions. As a result, they found that a Form II crystal can be obtained by adding and suspending Compound 1 into a certain organic solvent, and further found that the Form II crystal is superior in stability and oral absorbability compared to the Form I crystal, thereby completing the present invention.

Thus, the present invention relates to provision of the following [1] to [15].

[1] A Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide showing an X-ray powder diffraction spectrum having at least three characteristic diffraction peaks at angles (2θ±0.2°) selected from the group consisting of 7.7°, 8.0°, 11.1°, 12.5°, 12.9°, 15.2°, 15.8°, 17.2°, 19.0°, 22.5°, 26.1°, and 27.4°.

[2] The Form II crystal according to [1], wherein the crystal shows an X-ray powder diffraction spectrum having at least five characteristic diffraction peaks at angles (2θ±0.2°) selected from the group consisting of 7.7°, 8.0°, 11.1°, 12.5°, 12.9°, 15.2°, 15.8°, 17.2°, 19.0°, 22.5°, 26.1°, and 27.4°.

[3] The Form II crystal according to [1] or [2], wherein the endothermic peak determined by differential scanning calorimetry is around 270° C.

[4] A pharmaceutical composition comprising the Form II crystal according to any of [1] to [3].

[5] A pharmaceutical composition for oral administration comprising the Form II crystal according to any of [1] to [3].

[6] An antitumor agent comprising the Form II crystal according to any of [1] to [3].

[7] Use of the Form II crystal according to any of [1] to [3], for the production of a pharmaceutical composition.

[8] The use according to [7], wherein the pharmaceutical composition is a pharmaceutical composition for oral administration.

[9] Use of the Form II crystal according to any of [1] to [3], for the production of an antitumor agent.

[10] The Form II crystal according to any of [1] to [3], for use as a medicament.

[11] The Form II crystal according to any of [1] to [3], for use in the treatment of a tumor.

[12] A method of treating a tumor, comprising administering an effective amount of the Form II crystal according to any of [1] to [3] to a subject in need thereof.

[13] A method of manufacturing the Form II crystal according to any of [1] to [3], comprising the steps of:

(1) suspending the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide in an organic solvent with heating to obtain a suspension, and (2) obtaining solid-state 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide from the suspension obtained in the above step (1).

[14] The method of manufacturing the Form II crystal according to [13], wherein the organic solvent is 2-propanol, methyl acetate, ethyl acetate, propyl acetate, butyl acetate, cyclopentyl methyl ether, methyl ethyl ketone, methyl isobutyl ketone, acetone, acetonitrile or a mixed solvent thereof.

[15] A method of manufacturing the Form II crystal according to any of [1] to [3], comprising the steps of:

(1) suspending the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide in an organic solvent selected from the group consisting of 2-propanol, methyl acetate, ethyl acetate, propyl acetate, butyl acetate, cyclopentyl methyl ether, methyl ethyl ketone, methyl isobutyl ketone, acetone, acetonitrile and a mixed solvent thereof to obtain a suspension, and (2) obtaining solid-state 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide from the suspension obtained in the above (1).

Effect of the Invention

According to the present invention, the Form II crystal of Compound 1 has high stability and excellent oral absorbability, and is useful as an oral pharmaceutical.

DETAILED DESCRIPTION OF THE INVENTION

Compound 1 of the present invention is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide (represented by the below formula). Compound 1 is known to show HSP90 inhibitory activity and show excellent antitumor activity. Compound 1 can be synthesized based on the production method described in Patent Documents 1 and 2.

The crystal of the present invention may be a crystal comprising the Form II crystal of Compound 1, and may be a single crystal of the Form II crystal or a polymorphic mixture comprising crystals other than the Form II crystal. For the crystal of the present invention, the Form II crystal with high purity is preferred. Specifically, the chemical purity of the Form II crystal is preferably 90% or more, more preferably 95% or more, and particularly preferably 98% or more.

The Form II crystal of the present invention can be obtained by adding and suspending Compound 1 into a certain organic solvent. Specifically, the Form II crystal can be obtained by the production method comprising the following steps (1) and (2):

(1) suspending Compound 1 in an organic solvent to obtain a suspension, (2) obtaining solid-state Compound 1 from the suspension obtained in the above (1).

Although the Compound 1 to be added to an organic solvent may be a crystal or not, crystal form of the Compound 1 is preferably used and in particular the Form II crystal of the Compound 1 is preferably used from the viewpoint of obtaining the Form II crystal with high purity. In crystallization of the present invention, a seed crystal may be used. From the viewpoint of obtaining the Form II crystal with high purity, the Form II crystal is preferred for use as a seed crystal.

Examples of the organic solvent used in the crystallization of the present invention include alcohols such as methanol, n-propanol, 2-propanol and ethylene glycol; aliphatic carboxylate esters such as methyl acetate, ethyl acetate, propyl acetate, and butyl acetate; ethers such as diethyl ether, methyl tert-butyl ether, cyclopentyl methyl ether, 1,4-dioxane, tetrahydrofuran; ketones such as acetone, methyl ethyl ketone, methyl isobutyl ketone, and cyclohexanone; aromatic solvents such as toluene, xylene, and chlorobenzene; aprotic polar organic solvents such as acetonitrile, N-methyl-2-pyrrolidone, N,N-dimethylformamide, N,N-dimethylacetamide, 1,3-dimethyl-2-imidazolidinone, and dimethylsulfoxide or mixed solvents thereof. Preferably, the organic solvent is a ketone, a monohydric alcohol having 3 or more carbon atoms, a dihydric alcohol, an aliphatic carboxylate ester, an ether, an aprotic polar organic solvent or a mixed solvent thereof, and more preferably is 2-propanol, methyl acetate, ethyl acetate, propyl acetate, butyl acetate, cyclopentyl methyl ether, methyl ethyl ketone, methyl isobutyl ketone, acetone, acetonitrile or a mixed solvent thereof. Particularly preferably, from the viewpoint of purity and yield of the Form II crystal, the organic solvent is methyl acetate, methyl ethyl ketone, acetone or a mixed solvent thereof.

From the viewpoint of purity and yield of the Form II crystal, the amount (v/w) of the organic solvent in the crystallization of the present invention is preferably 2-30 times amount, more preferably 3-20 times amount, and particularly preferably 4-15 times amount, relative to the amount of Compound 1.

Preferably, in the crystallization of the present invention, Compound 1 is added and suspended into an organic solvent with heating and refluxed for a long time. The heating temperature in the crystallization of the present invention is not specifically limited as long as it falls within the temperature suitable for reflux, and is appropriately determined depending on the organic solvent used. Preferably, the heating temperature is 52-126° C.

The duration of reflux in the crystallization of the present invention is preferably 12-60 hours and more preferably 16-48 hours, otherwise, crystallization dose not sufficiently proceed and thus a high purity crystal cannot be obtained in shorter duration, and on the other hand, degradation of the crystal occurs and leads to low yield in longer duration.

In the crystallization of the present invention, precipitate of Form II crystal after cooling can be collected after reflux. Cooling temperature may be appropriately adjusted, is preferably room temperature.

The precipitate of the crystal can be isolated and purified from said dissolution or mixed solution according to known separation and purification methods such as, for example, filtration, washing by an organic solvent, and drying under reduced pressure.

Examples of the organic solvent used for the washing include lower alcohols, acetone, and acetonitrile. The organic solvent used in Form II crystallization may be used for washing.

Figure 2:
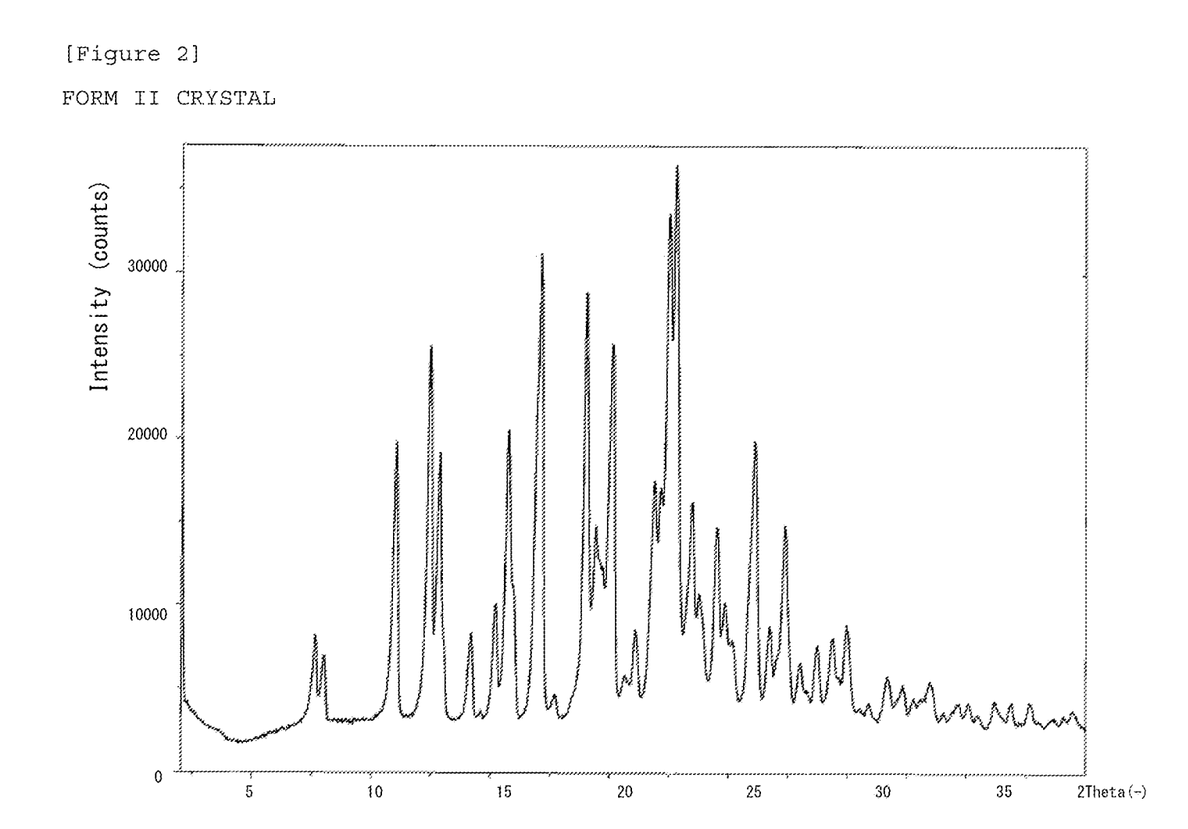
FIG. 2 An X-ray powder diffraction spectrum of the Form II crystal of Compound 1 (the vertical axis represents intensity (cps) and the horizontal axis represents the diffraction angle (2θ±0.2°)).
Figure 3:
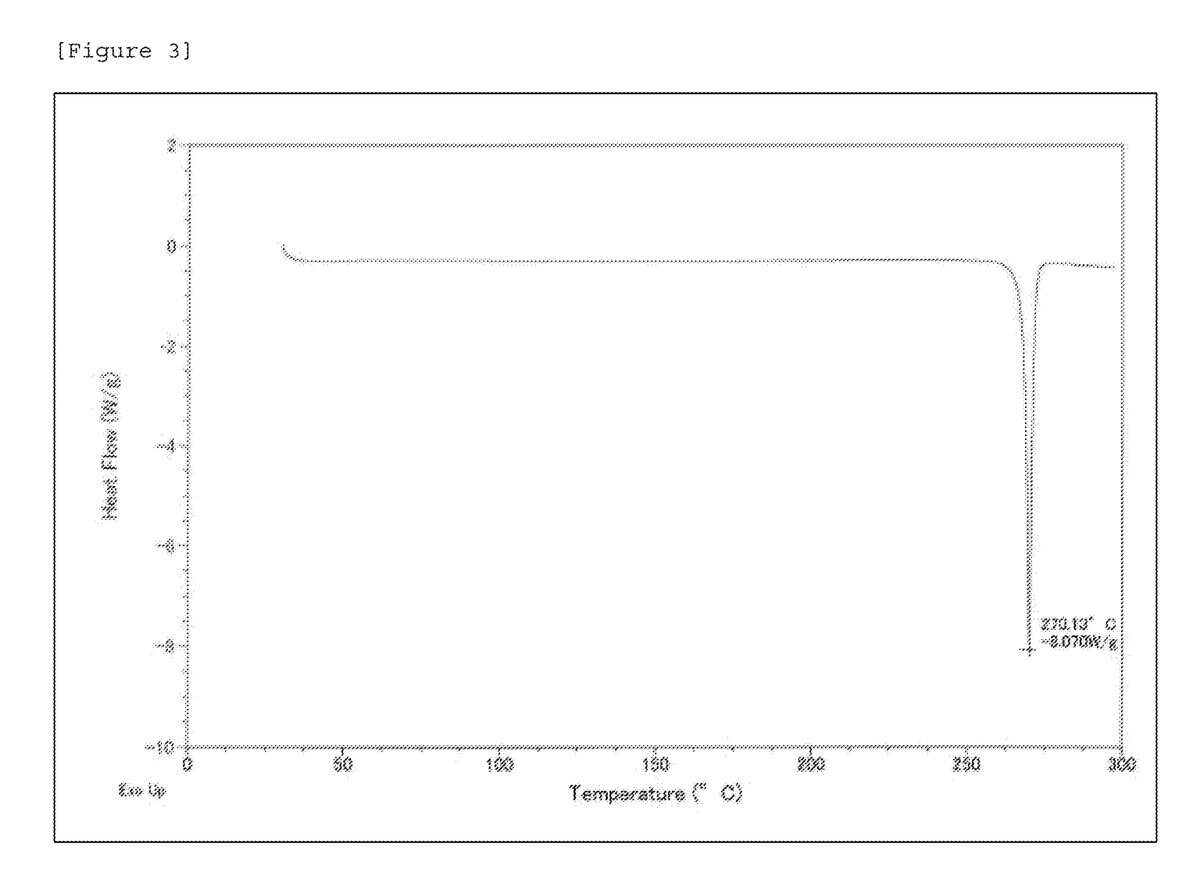
FIG. 3 A differential scanning calorimetry (DSC) curve of the Form II crystal of Compound 1.

The Form II crystal of the present invention thus obtained is a crystal showing an X-ray powder diffraction spectrum having 3 or more, preferably 5 or more, more preferably 8 or more, and still more preferably 12 or more characteristic diffraction peaks at angles (2θ±0.2°) selected from the group consisting of 7.7°, 8.0°, 11.1°, 12.5°, 12.9°, 15.2°, 15.8°, 17.2°, 19.0°, 22.5°, 26.1°, and 27.4°, as shown in FIG. 2. The Form II crystal shows an endothermic peak around 270° C., as shown in the result of differential scanning calorimetry (DSC) in FIG. 3.

Figure 1:
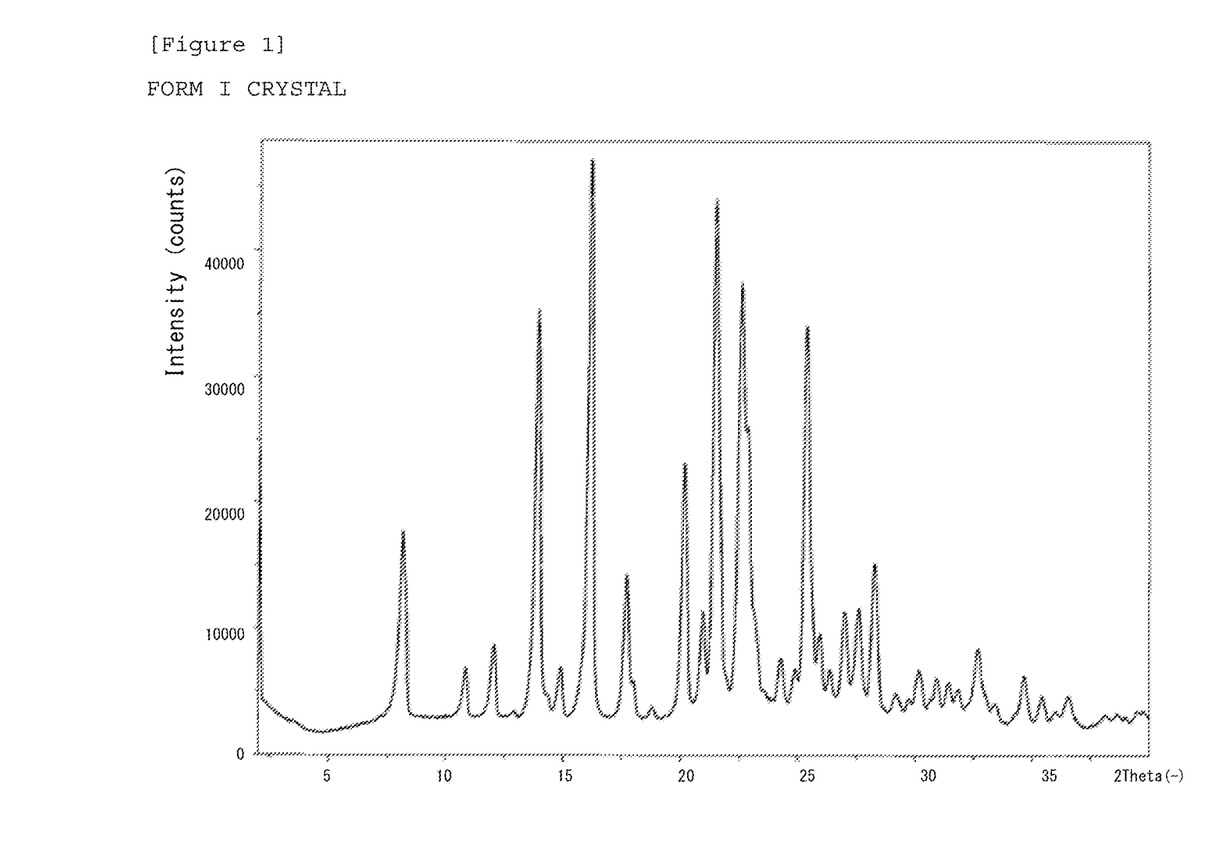
FIG. 1 An X-ray powder diffraction spectrum of the Form I crystal of Compound 1 (the vertical axis represents intensity (cps) and the horizontal axis represents the diffraction angle (2θ±0.2°)).

In contrast, the Form I crystal is a crystal showing an X-ray powder diffraction spectrum having characteristic diffraction peaks at angles (2θ±0.2°) of 8.1°, 12.1°, 14.0°, 16.2°, 21.5°, 25.4° and 28.3°, as shown in FIG. 1.

Peak values in an X-ray powder diffraction spectrum may involve some errors due to measuring instruments or measuring conditions such as reading conditions of peaks. The peak values in the specification of the present application may have measurement errors in the range of around ±0.2°.

The endothermic peak (a peak top value) measured in differential scanning calorimetry may fluctuate depending on the increase of temperature per minute, the amount of samples and purity etc. The term "around" in the specification of the present application refers to ±5.0° C.

As shown in Examples below, the Form I crystal and the Form II crystal of Compound 1 have significantly different absorbability on oral administration. The result that the Form II crystal, a stable form, shows higher oral absorbability compared to the Form I crystal, a metastable form, is an unexpected result because a metastable form in general has higher solubility than a stable form (Akira Tsuji, "New pharmaceutics", published from NANKODO Co. Ltd.).

The Form I crystal of Compound 1 changes to the Form II crystal by refluxing. The Form II crystal is stable in high temperature conditions and high humidity conditions. Therefore, the Form II crystal is stable compared to the Form I crystal and useful as a pharmaceutical material.

Therefore, the Form II crystal of the present invention is useful as an effective ingredient of a pharmaceutical composition and in particular useful as an effective ingredient of pharmaceutical composition for oral administration. The Form II crystal of the present invention is useful as an antitumor agent, because Compound 1 shows excellent HSP90 inhibitory activity. Target cancers for treatment include, without limitation, head and neck carcinoma, gastrointestinal carcinoma (such as esophageal carcinoma, gastric cancer, gastrointestinal stromal tumor, duodenal carcinoma, hepatocarcinoma, biliary carcinoma (such as gallbladder-bile duct cancer), pancreatic cancer, small intestine carcinoma, and large bowel cancer (such as colorectal carcinoma, colon cancer, and rectal cancer)), lung carcinoma, breast carcinoma, ovarian cancer, uterine carcinoma (such as cervical cancer, and endometrial cancer), kidney carcinoma, bladder cancer, prostate cancer, urothelial carcinoma, bone and soft tissue sarcoma, blood cancer (such as B-cell lymphoma, chronic lymphocytic leukemia, peripheral T-cell lymphoma, myelodysplastic syndrome, acute myeloid leukemia, and acute lymphocytic leukemia), multiple myeloma, skin cancer, and mesothelioma.

When the Form II crystal of the present invention is used as an active ingredient of a pharmaceutical composition, it may be blended with a pharmaceutically acceptable carrier as needed and a variety of administration forms may be employed depending on preventive or therapeutic purposes. Said forms are preferably an oral agent such as a tablet, a capsule, a granule, a subtle granule, and a powdered drug. Each of these administration forms can be manufactured by methods for drug formulation known to those skilled in the art.

EXAMPLES

Although the present invention is specifically described below with reference to Examples, the present invention shall not be limited by these embodiments. Although the present invention is sufficiently described by Examples, it should be understood that various changes and modifications can be made by those skilled in the art. Therefore, such changes and modifications are encompassed by the present invention, as long as they do not depart from the scope of the present invention.

Reagents used in Examples were commercially available, unless otherwise specified. A NMR spectrum was measured by using tetramethylsilane as an internal standard when tetramethylsilane is included in a deuterated solvent and using a NMR solvent as an internal standard otherwise, using AL400 (400 MHz; Japan Electro Optical Laboratory (JEOL)), Mercury 400 (400 MHz; Agilent Technologies) model spectrometer, or Inova 400 (400 MHz; Agilent Technologies) model spectrometer equipped with 400MNMR probe (Protasis). All δ values are indicated in ppm.

The meanings of abbreviation are shown below.
s: Singlet
d: Doublet
t: Triplet
q: Quartet
dd: Double Doublet
dt: Double Triplet
td: Triple Doublet
tt: Triple Triplet
ddd: Double Double Doublet
ddt: Double Double Triplet
dtd: Double Triple Doublet
tdd: Triple Double Doublet
m: Multiplet
br: Broad
brs: Broad Singlet
X-Ray Powder Diffraction Measurement X-ray powder diffraction was measured in accordance with the following test conditions after lightly pulverizing a suitable amount of test material by using an agate mortar as needed.
Instrument: PANalytical EMPYREAN
Target: Cu
X-ray output setting: 40 mA, 45 kV
Scanning range: 2.0-40.0°
Step size: 0.026°
Divergence slit: automatic
Irradiation width: 10.00 mm
Sample width: 10.00 mm Handling of instruments including data processing was performed in accordance with the method and procedure indicated by each instruments.

Thermal Analysis Measurement (Differential Scanning Calorimetry (DSC))

DSC was performed in accordance with the following test conditions.
Instrument: TA Instruments Q1000
Sample: around 1 mg
Sample container: made of aluminum
Heating rate: heating at 10° C./min to 300° C.
Atmosphere gas: Nitrogen
Nitrogen gas flow rate: 50 mL/min.

Handling of instruments including data processing was performed in accordance with the method and procedure indicated by each instruments.

Comparative Example 1: Synthesis of the Form I crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (3.58 g) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to ethanol (7.84 mL) and stirred for 2 hours at room temperature. After collecting the solid by filtration, the solid was washed with ethanol (7.84 mL), followed by drying under reduced pressure at 70-80° C. for 20 hours to obtain the Form I crystal (yield: 2.40 g, percent yield: 61.2%, purity: 98.21%).

The Form I crystal gave an X-ray powder diffraction spectrum having characteristic peaks at diffraction angles (2θ) of 8.1°, 10.9°, 12.1°, 14.0°, 14.9°, 16.2°, 17.7°, 20.2°, 21.0°, 21.5°, 22.6°, 24.3°, 25.4°, 26.4°, 27.0°, 28.3°, 30.2°, 30.9°, 31.5°, 32.7°, 34.7°, 35.4° and 36.6°, as shown in FIG. 1.

$^1$H-NMR (DMSO-$d_6$): δ ppm 9.35 (1H, d, J=4.88 Hz), 8.93 (1H, d, J=1.22 Hz), 8.84 (1H, brs), 8.72 (1H, d, J=1.95 Hz), 8.70 (1H, s), 8.63 (1H, d, J=1.22 Hz), 8.60 (1H, dd, J=8.29, 1.95 Hz), 8.46 (1H, s), 8.25 (1H, d, J=8.29 Hz), 8.22 (1H, brs), 8.12 (1H, d, J=4.88 Hz), 4.59 (3H, s), 3.95 (1H, tt, J=6.83, 6.83 Hz), 3.21 (2H, q, J=7.56 Hz), 1.83 (6H, d, J=6.83 Hz), 1.75 (3H, t, J=7.56 Hz): LRMS (ESI) m/z 455 [M+H]

Example 1: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (4.0 g) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to acetone (19.54 mL) and stirred for 16 hours by heating under reflux. After allowing the mixture to cool to room temperature, the solid was collected by filtration and washed with acetone (8.4 mL), followed by drying under reduced pressure at 70-80° C. for 16-24 hours to obtain the Form II crystal (yield: 1.59 g, percent yield: 57.0%, purity 98.37%).

The Form II crystal gave an X-ray powder diffraction spectrum having characteristic peaks at diffraction angles (2θ) of 7.7°, 8.0°, 11.1°, 12.5°, 12.9°, 14.2°, 15.2°, 15.8°, 17.2°, 17.7°, 19.0°, 20.2°, 21.1°, 22.5°, 22.8°, 23.5°, 24.5°, 26.1°, 26.7°, 27.4°, 28.0°, 28.7°, 29.4°, 30.0°, 31.7°, 35.1°, 36.2°, 36.9° and 37.6°, as shown in FIG. 2. The Form II crystal showed an endothermic peak around 270° C., as shown in the result of differential scanning calorimetry (DSC) in FIG. 3.

$^1$H-NMR (DMSO-$d_6$): δ ppm 9.35 (1H, d, J=4.88 Hz), 8.93 (1H, d, J=1.22 Hz), 8.84 (1H, brs), 8.72 (1H, d, J=1.95 Hz), 8.70 (1H, s), 8.63 (1H, d, J=1.22 Hz), 8.60 (1H, dd, J=8.29, 1.95 Hz), 8.46 (1H, s), 8.25 (1H, d, J=8.29 Hz), 8.22 (1H, brs), 8.12 (1H, d, J=4.88 Hz), 4.59 (3H, s), 3.95 (1H, tt, J=6.83, 6.83 Hz), 3.21 (2H, q, J=7.56 Hz), 1.83 (6H, d, J=6.83 Hz), 1.75 (3H, t, J=7.56 Hz): LRMS (ESI) m/z 455 [M+H]

Example 2: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to methyl ethyl ketone (2.8 mL) and stirred for 16 hours by heating under reflux. After allowing the mixture to cool to room temperature, the solid was collected by filtration and washed with methyl ethyl ketone (1.2 mL), followed by drying under reduced pressure at 70-80° C. for 16-24 hours to obtain the Form II crystal (yield: 197 mg, percent yield: 60.9%, purity 98.83%).

Example 3: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to acetonitrile (4.0 mL) and stirred for 3 hours by heating under reflux. After allowing the mixture to cool to room temperature, the solid was collected by filtration and washed with acetonitrile (1.2 mL), followed by drying under reduced pressure at 70-80° C. for 3 hours to obtain the Form II crystal (yield: 120 mg, percent yield: 43.0%, purity 98.25%).

Example 4: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to methyl isobutyl ketone (4.0 mL) and stirred for 3 hours by heating under reflux. After allowing the mixture to cool to room temperature, the solid was collected by filtration and washed with methyl isobutyl ketone (1.2 mL), followed by drying under reduced pressure at 70-80° C. for 3 hours to obtain the Form II crystal (yield: 154 mg, percent yield: 55.3%, purity 96.89%).

Example 5: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to 2-propanol (4.0 mL) and stirred for 3 hours by heating under reflux. After allowing the mixture to cool to room temperature, the solid was collected by filtration and washed with 2-propanol (1.2 mL), followed by drying under reduced pressure at 70-80° C. for 3 hours to obtain the Form II crystal (yield: 108 mg, percent yield: 38.8%, purity 96.83%).

Example 6: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to ethyl acetate (4.0 mL) and stirred for 3 hours by heating under reflux. After allowing the mixture to cool to room temperature, the solid was collected by filtration and washed with ethyl acetate (1.2 mL), followed by drying under reduced pressure at 70-80° C. for 3 hours to obtain the Form II crystal (yield: 156 mg, percent yield: 56.0%, purity 96.45%).

Example 7: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to butyl acetate (4.0 mL) and stirred for 3 hours by heating under reflux. After allowing the mixture to cool to room temperature, the solid was collected by filtration and washed with butyl acetate (1.2 mL), followed by drying under reduced pressure at 70-80° C. for 3 hours to obtain the Form II crystal (yield: 164 mg, percent yield: 58.8%, purity 96.04%).

Example 8: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to cyclopentyl methyl ether (4.0 mL) and stirred for 3 hours by heating under reflux. After allowing the mixture to cool to room temperature, the solid was collected by filtration and washed with cyclopentyl methyl ether (1.2 mL), followed by drying under reduced pressure at 70-80° C. for 3 hours to obtain the Form II crystal (yield: 192 mg, percent yield: 68.8%, purity 95.68%).

Example 9: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to propyl acetate (4.0 mL) and stirred for 3 hours by heating under reflux. After allowing the mixture to cool to room temperature, the solid was collected by filtration and washed with propyl acetate (1.2 mL), followed by drying under reduced pressure at 70-80° C. for 3 hours to obtain the Form II crystal (yield: 172 mg, percent yield: 61.5%, purity 96.77%).

Example 10: Synthesis of the Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide A white solid (400 mg) of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide obtained according to the method of manufacturing described in International Publication No. WO2012/093708 pamphlet and International Publication No. WO2011/004610 pamphlet was added to methyl acetate (2.2 mL) and stirred for 16 hours by heating under reflux. After allowing the mixture to cool to room temperature, the solid was collected by filtration and washed with methyl acetate (0.94 mL), followed by drying under reduced pressure at 80° C. to obtain the Form II crystal (yield: 215.5 mg, percent yield: 68.6%, purity 98.06%).

Test Example 1: Blood Concentration Measurement Test

Respective solutions for administration (50 mg/10 mL/kg) of the Form I crystal and Form II crystal were produced. These solutions were administered orally to mice (Balb/cA) bred under feeding conditions at a volume of 10 mL/kg body weight using a sonde for oral administration. After the administration, the mice were returned to cages for mice to inspect their conditions. Water and feed were freely available for the mice in the cages. The mice were anesthetized with isoflurane 1, 2, 3, 4, 8 and 24 hours after the administration and 60 μL of blood was collected from their orbital sinuses using capillary blood collection tubes. The collected blood was cooled on ice and centrifuged to separate plasma.

$AUCs_{0-24\ hr}$ were calculated with a linear-log trapezoid method using Phoenix WinNonlin (v6.3.0), software from Pharsight, from the concentrations of Compound 1 in plasma samples measured with Multiple Reaction Monitoring method using LC-MS/MS.

Figure 4:
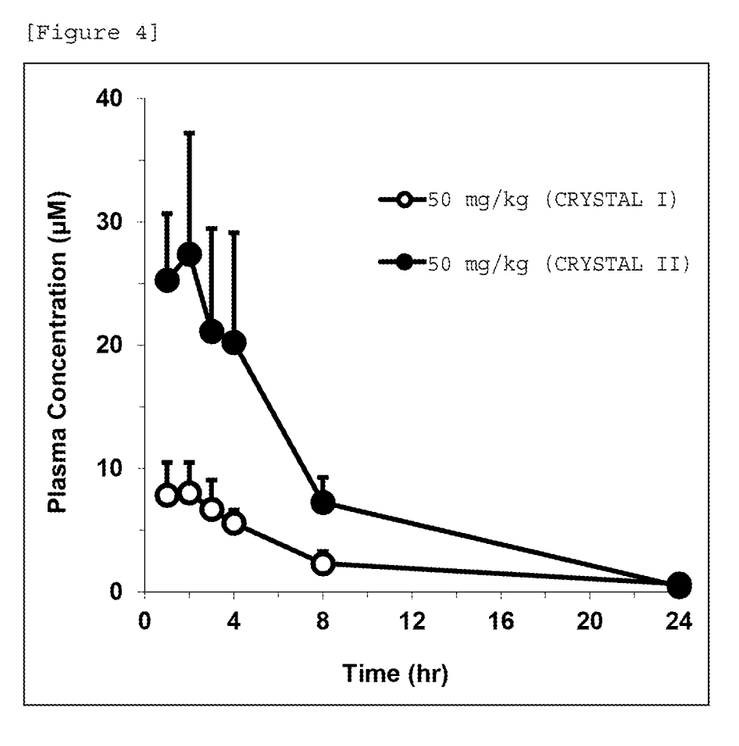
FIG. 4 A result of blood concentration measurement test of the Form II crystal of Compound 1.

Results are shown in FIG. 4 and Table 1. This test proved that the $AUC_{0-24\ hr}$ (area under the concentration in blood-time curve 0-24 hours after the administration) of the Form II crystal was approximately 3 times higher than that of the Form I crystal. Therefore, the Form II crystal according to the present invention is remarkably excellent in oral absorbability and useful as an oral pharmaceutical composition.

TABLE 1

| Parameter | Oral administration | |
|---|---|---|
| | Form I crystal | Form II crystal |
| $AUC_{0-24\ hr}$ (μM · hr) | 59.64 | 171.33 |

Test Example 2: Solid Stability Test (Accelerated Test)

The solid stability of the Form II crystal obtained in Example 1 after storage of 1, 3 and 6 months at 40° C.±2° C./75% RH±5% RH was measured under the following conditions.
Storage conditions: 40° C.±2° C./75% RH±5% RH
Measurement points: 1, 3 and 6 month
Storage amount: 6 g
Storage container: doubled plastic bags, banding bands+ plastic drums
Preparation method of sample solution: 100 mg of the Form II crystal is accurately measured, a mixed solution of acetonitrile-water (4:1) is added to dissolve the crystal (sonicated to dissolve, if difficult to dissolve), and the solution is diluted in measuring cylinder to exact 200 mL total. 10 mL of this solution is accurately measured, and a mixed solution of acetonitrile-water (1:1) is added to exact 20 mL to be used as a sample solution.
HPLC was performed in the following conditions.
Column: general foundation Chemicals Evaluation and Research Institute, Japan L-column2 ODS
Particle size: 3 μm, Inner diameter: 4.6 mm, Length: 15 cm
Measurement wavelength: 220 nm
Mobile phase: Mobile phase A: 10 mmol/L phosphate buffer (pH6.9),
Mobile phase B: acetonitrile
Flow rate: about 1.0 mL/min
The concentration gradient is controlled by changing the mixing ratio of mobile phases A and B as follows, when feeding the liquid.

TABLE 2

| Time (min) after injection | Mobile phase A (%) | Mobile phase B (%) |
|---|---|---|
| 0 to 25 | 80 | 20 |
| 25 to 45 | 80 → 65 | 20 → 35 |
| 45 to 55 | 65 | 35 |

TABLE 2-continued

| Time (min) after injection | Mobile phase A (%) | Mobile phase B (%) |
|---|---|---|
| 55 to 70 | 65 → 10 | 35 → 90 |
| 70 to 80 | 10 | 90 |
| 80 to 80.1 | 10 → 80 | 90 → 20 |
| 80.1 to 95 | 80 | 20 |

The amounts of related substances in the sample solutions were measured and evaluated by HPLC, of which result is shown in Table 3.

The related substances are defined as substances detected other than 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

TABLE 3

| | 1 month | 3 months | 6 months |
|---|---|---|---|
| Related substances in the Form II crystal | less than 0.1% | less than 0.1% | less than 0.1% |

As apparent from this result, the Form II crystal of Compound 1 produces a low amount of related substances and shows excellent solid stability.

The invention claimed is:

1. A Form II crystal of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide showing an X-ray powder diffraction spectrum having at least five characteristic diffraction peaks at angles (2θ+0.2°) selected from the group consisting of 7.7°, 8.0°, 11.1°, 12.5°, 12.9°, 15.2°, 15.8°, 17.2°, 19.0°, 22.5°, 26.1°, and 27.4°.

2. The Form II crystal according to claim 1, wherein an endothermic peak determined by differential scanning calorimetry is around 270° C.

3. A pharmaceutical composition comprising:
the Form II crystal according to claim 1, and
a pharmaceutically acceptable carrier.

4. The pharmaceutical composition of claim 3, which is suitable for oral administration.

5. The pharmaceutical composition of claim 3, which has an antitumor activity.

6. A method of manufacturing the Form II crystal according to claim 1, comprising:
(1) suspending 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide in an organic solvent with heating to obtain a suspension, and
(2) obtaining solid-state 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide from the suspension obtained in (1),
wherein the organic solvent is 2-propanol, methyl acetate, ethyl acetate, propyl acetate, butyl acetate, cyclopentyl methyl ether, methyl ethyl ketone, methyl isobutyl ketone, acetone, acetonitrile or a mixture thereof.

* * * * *

UNITED STATES PATENT AND TRADEMARK OFFICE
CERTIFICATE OF CORRECTION

PATENT NO. : 10,526,324 B2
APPLICATION NO. : 15/572398
DATED : January 7, 2020
INVENTOR(S) : Takao Uno Page 1 of 1

It is certified that error appears in the above-identified patent and that said Letters Patent is hereby corrected as shown below:

In the Specification

Column 2, Line 1:
"diffraction peaks at angles (28 ± 0.2°) selected from the group"
Should read as:
--diffraction peaks at angles ($2\theta \pm 0.2°$) selected from the group--

Column 2, Line 7:
"(28 ± 0.2°) selected from the group consisting of 7.7°, 8.0°"
Should read as:
--($2\theta \pm 0.2°$) selected from the group consisting of 7.7°, 8.0°--

Column 12, Line 33:
"fraction peaks at angles ($2\theta + 0.2°$) selected from the group"
Should read as:
--fraction peaks at angles ($2\theta \pm 0.2°$) selected from the group--

Signed and Sealed this
Twenty-fourth Day of November, 2020

Andrei Iancu
*Director of the United States Patent and Trademark Office*